United States Patent [19]

Feinberg et al.

[11] Patent Number: 5,313,315
[45] Date of Patent: May 17, 1994

[54] METHOD OF IMAGING THROUGH A SCATTERING MEDIUM USING COHERENT LIGHT

[75] Inventors: Jack L. Feinberg, Manhattan Beach, Calif.; Alexander Rebane, Zürich, Switzerland

[73] Assignee: University of Southern California, Los Angeles, Calif.

[21] Appl. No.: 880,170

[22] Filed: May 6, 1992

[51] Int. Cl.$^5$ .................... G03H 1/02; G03H 1/14; G03C 1/00
[52] U.S. Cl. .......................................... 359/4; 359/3; 430/2
[58] Field of Search ............... 365/119, 125; 358/95, 358/99; 359/1, 3, 4; 430/2

[56] References Cited

U.S. PATENT DOCUMENTS

| | | | |
|---|---|---|---|
| 4,174,524 | 11/1979 | Moran | 358/95 |
| 4,459,682 | 7/1984 | Mossberg | 365/119 |
| 5,191,574 | 3/1993 | Henshaw et al. | 365/119 |

OTHER PUBLICATIONS

A. Rebane et al, "Time-resoved holography", in *NATURE*, vol. 351, pp. 378-380 (May 30, 1991).

L. Wang, et al, "Ballistic 2-D Imaging Through Scattering Walls Using an Ultrafast Optical Kerr Gate", in *REPORTS*, pp. 769-771 (Aug. 16, 1991) SCIENCE.

H. Chen, et al, "Two-dimensional imaging through diffusing media using 150-fs gated electronic holography techniques", in *OPTICAL*, vol. 16, No. 7, pp. 487-489 (Apr. 1, 1991).

K. M. Yoo et al, "Time-resolved coherent and incoherent components of forward light scattering in random media", in *OPTICAL*, vol. 15, No. 6, pp. 320-322 (Mar. 15, 1990).

Kenneth G. Spears et al, "Chrono-Coherent Imaging for Medicine", in *IEEE*, vol. 36, No. 12, pp. 1210-1221 (Dec. 1989).

Nils H. Abramson et al, "Single pulse Light-in-flight recording by holography", in *APPLIED OPTICS*, vol. 28, No. 10, pp. 1834-1841 (May 15, 1989).

Tung H. Jeong, "Progress in Pictorial Holography", in *LASER FOCUS/ELECTRO-OPTICS*, pp. 77,78,80,82,84,86,88 & 89 (Apr. 1984).

*Primary Examiner*—Loha Ben
*Assistant Examiner*—John Juba, Jr.
*Attorney, Agent, or Firm*—Benman Collins & Sawyer

[57] ABSTRACT

In a conventional hologram, a photographic film records the interference pattern of monochromatic light, scattered from an object (20) to be imaged, with a reference beam of unscattered light. Illumination of the developed film with a replica of the reference beam then creates a virtual image of the original object. Molecular resonance may be used to record an interference pattern between light signals that arrive at different times, and with this technique create a hologram (10') with time resolution. Using a time reference pulse (16) as a "light shutter", holographic images may be recorded selectively, according to the time taken by light travelling from the object to the hologram. This method may be used to image an object obscured by a light-scattering medium.

22 Claims, 3 Drawing Sheets

FIG. 1A
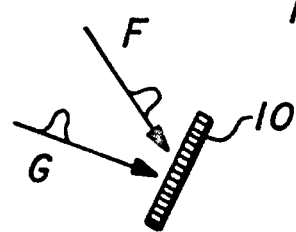
FIG. 1B
FIG. 1C
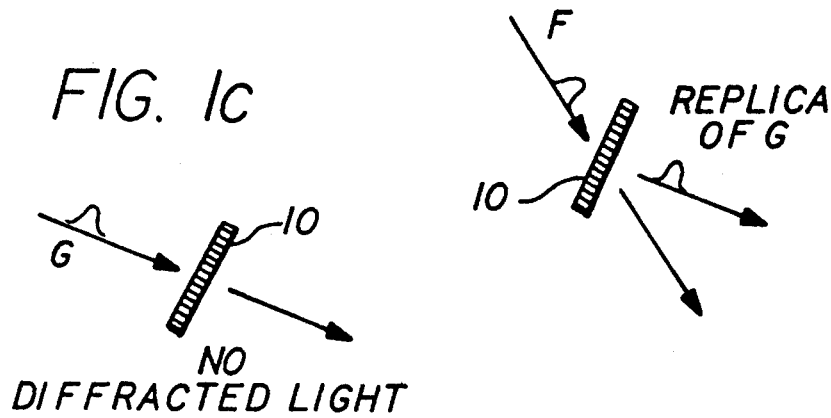
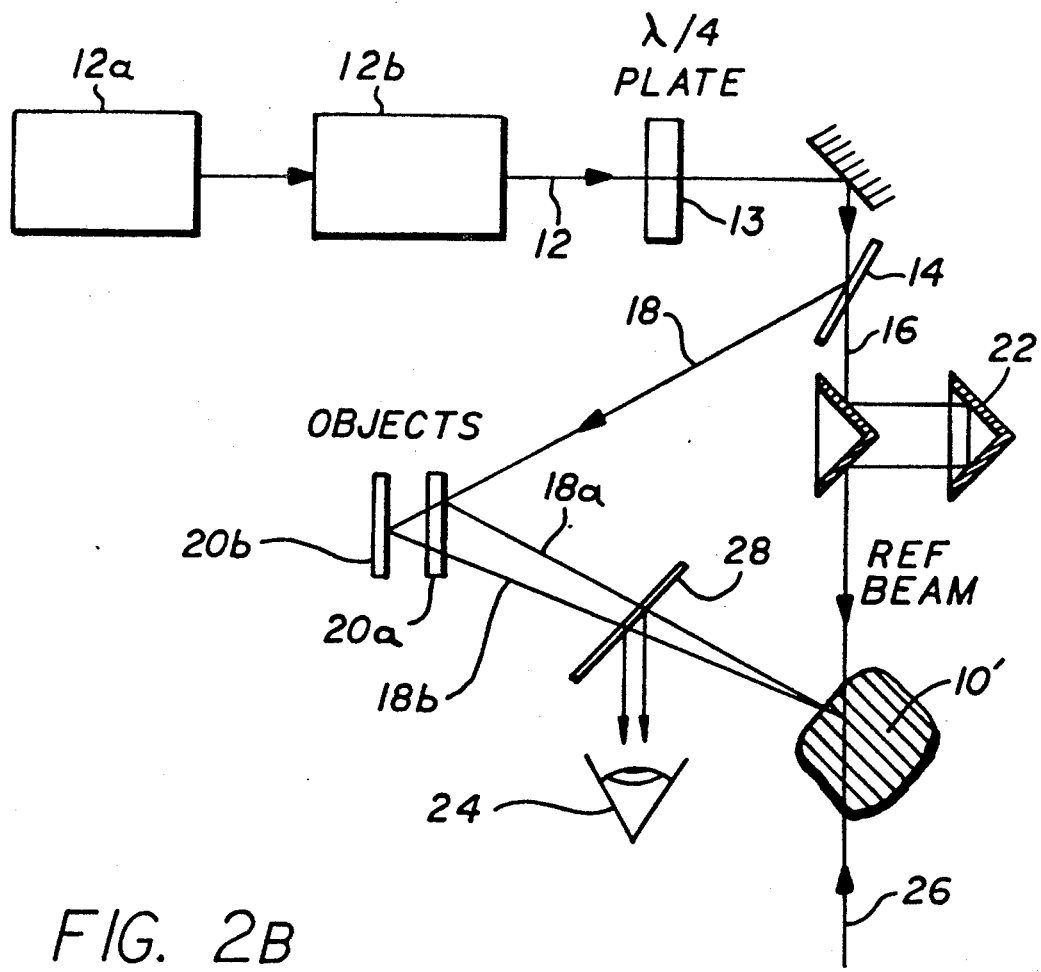
FIG. 2B

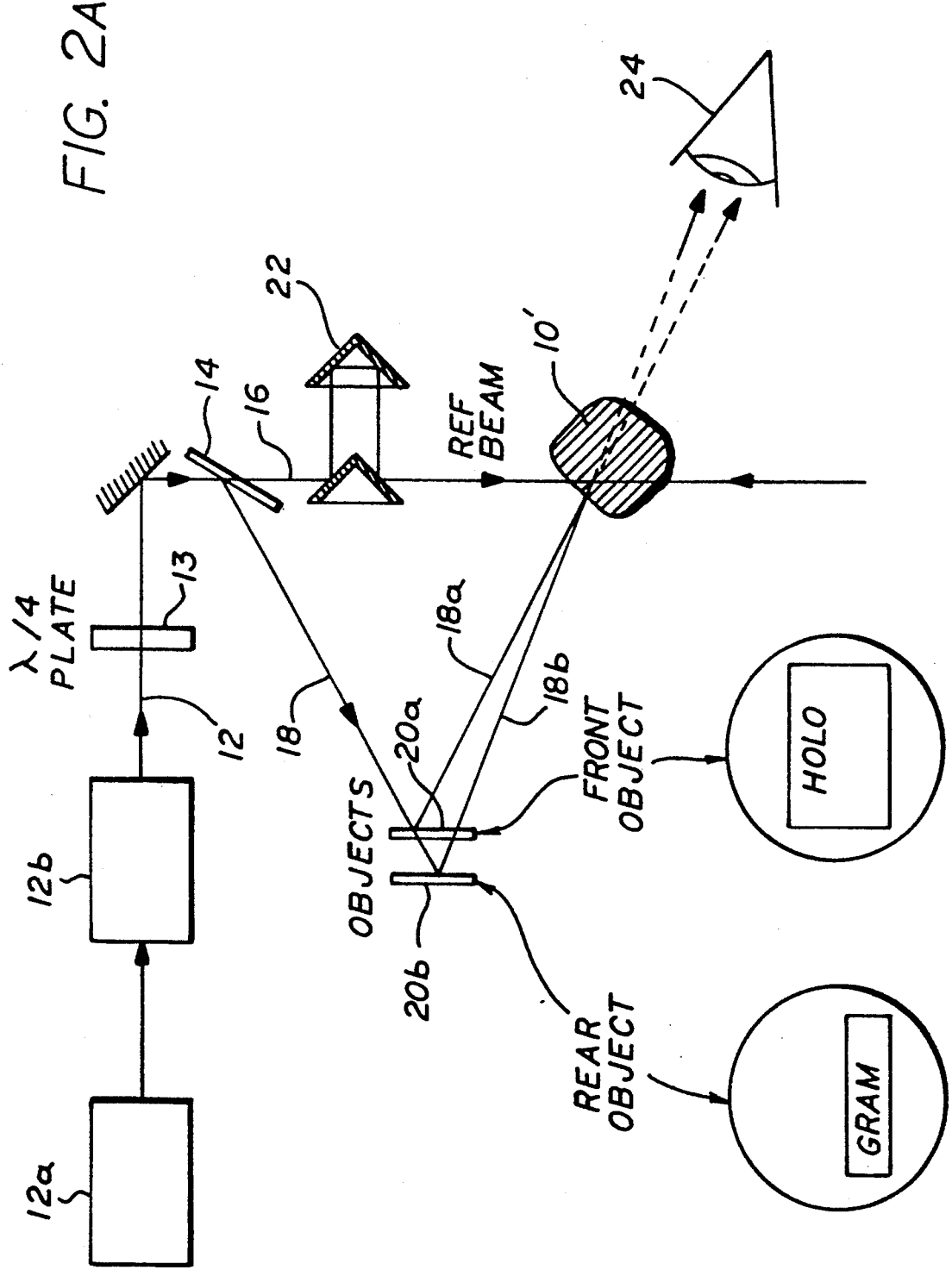

METHOD OF IMAGING THROUGH A SCATTERING MEDIUM USING COHERENT LIGHT

ORIGIN OF THE INVENTION

The present invention was made with government support under contract F49620-88-C-0095 awarded by the U.S. Air Force Office of Scientific Research. The government has certain rights in the invention.

TECHNICAL FIELD

The present invention relates to imaging, and, in particular, to a method of imaging an object obscured by a light-scattering medium, using coherent light.

BACKGROUND ART

Attempts to illuminate an object embedded in or hidden by a light-scattering medium are often difficult to accomplish reasonably. For example, while X-rays may be employed to image bones, the high energy of X-rays limits their usefulness due to potential damage to tissue. Also, in the detection of breast cancer in women, present mammography requires exposure of breast tissue to X-rays; this procedure, repeated several times over the course of a woman's man's life, has its own risks of creating cancer, even though the benefits may outweigh the risks.

As a general rule, light, though of a lower energy and thus not as damaging to tissue, cannot be used to image such objects. This is due to the fact that most of the light going through a light-scattering medium, such as flesh, is scattered; only a small fraction of the incident light is not scattered.

Suppose one wanted to view a light-absorbing object embedded in or behind a light-scattering medium. If it were possible to see an image of such an object, the image would appear as a shadow-gram of the object. However, in general, the light scattered by the medium fills in the shadow of the object produced by the unscattered light, thus making the object invisible.

A key fact is that the portion of light that is not scattered emerges first from the light-scattering medium, while the scattered light emerges later. One could use this fact to produce an image of the object, if one could somehow provide a shutter to separate the light that is scattered from that which is not. Note, however, that the time resolution of such a shutter, which depends on the sample thickness, must be on the order of $10^{-12}$ seconds, or 1 pico-second (ps). Such a requirement eliminates mechanical shuttering, which cannot physically respond in such short times.

One approach provided by the prior art is to use a Kerr shutter. Such a device incorporates a cell of a liquid, such as $CS_2$, positioned between two polarizers, set orthogonal to each other so that light incident on one polarizer does not pass through the other. When an intense beam of light is directed onto the liquid cell, the intense beam disturbs the polarization of light passing through the cell, so that light incident on the one polarizer can now pass through the other polarizer. When the intense beam is turned off, the liquid relaxes back to its original state, and the light is again blocked by the pair of polarizers. The typical relaxation time for this method is about 1 ps.

Another approach in the prior art is known as "light-in-flight" (LIF) recording by holography, developed by N. Abramson and co-workers. In this method, a short coherence length pulse is split into two parts and geometrically ar ranged to both illuminate an object and scan a reference beam across a holographic plate so that holographic images can be formed in a continuous time sequence across the plate. A related approach, called "chrono-coherent imaging" (CCI) is an adaptation of LIF recording to medical imaging. Unlike LIF recording, which is done in air, medical imaging applications have a liquid medium and do not emphasize reflectivity of solid objects. The imaging modality is differential reflectivity or absorption, and it involves the effects of shadows from differential absorption (or differential scattering). In both cases, wavefronts interfere in successive times to produce a hologram that, when viewed along its length, recreates the time sequence.

Like the Kerr shutter, the LIF and CCI techniques also isolate the first-arriving light, and provide jitter-free, low-power, high-pulse-repetition-rate, two-dimensional imagery, with a temporal resolution virtually the same as the pulse duration. However, the LIF-type configuration does not necessarily produce the best spatial resolution, especially with short pulse durations in the femtosecond domain.

A variation of the holographic recording method is to replace the photographic recording plate by a high-resolution electronic camera. The camera records the hologram, which can then be sent to a computer for analysis; see, e.g., Chen et al, *Optics Letters*, Vol. 16, No. 7, pp. 487–489 (1991).

Another method for isolating the first-arriving light is to use the process of second-harmonic generation; see, e.g., Yoo et al, *Optics Letters*, Vol. 16, No. 13, pp. 1019–1021 (1991). In this method, a short pumping pulse of frequency $\omega$ and photons from the scattering medium (also at frequency $\omega$) are made to overlap in a frequency-doubling crystal. If photons from the two light sources reach the crystal at the same instant, then the crystal will emit a photon of frequency $2\omega$ in a particular direction. This frequency-doubled light is easily detected. (If the photons do not reach the crystal at the same time, then, in principal, no frequency-doubled light is observed.) The pump pulse is adjusted to arrive at the crystal at the same time as the unscattered light from the scattering medium, so that the amount of frequency-doubled light is proportional to the amount of unscattered light reaching the crystal. The sample is scanned, point by point, and the amount of frequency-doubled light is recorded for each point in the sample. In this way, a two-dimensional image of the unscattered light is laboriously constructed. A disadvantage of this scheme is that the entire image cannot be acquired at the same time; instead, the sample must be slowly scanned, point by point.

A need remains for a technique for storing and producing images of an object obscured by a light-scattering medium, using light.

DISCLOSURE OF INVENTION

In accordance with the invention, a method is provided for producing an image of an object obscured by a light-scattering medium. The image is stored in a spectral hole-burning material by the following sequence of steps:

(a) providing a coherent source of light of sufficiently broad spectral content to illuminate the spectral hole-burning material, the source of light generating a source beam, (b) splitting the source beam into two portions, a reference beam and an object beam, (c) directing the reference beam onto the spectral hole-burning material, (d) directing the object beam onto the light-scattering medium to generate an image-bearing beam which is by predetermined choice either transmitted through the light-scattering medium or reflected thereby, and (e) directing the image-bearing beam onto the spectral hole-burning material in a manner so as to interact with the reference beam within a predetermined time related to $1\ \Delta\omega$ for a time sufficient to alter the hole-burning material to cause the appearance of narrow spectral holes, having a width $\Delta\omega$, in its absorption spectrum to thereby expose the hole-burning material and store the image therein.

It should be noted that the difference between the present invention, which employs spectral hole-burning materials, and previous holographic and non-holographic methods is that the reference beam and the image-bearing beam should not arrive at the same place at the same time in order to record the information.

The stored image of the object may be produced by illuminating the exposed hole-burning material with light and observing any diffracted light.

BRIEF DESCRIPTION OF THE DRAWINGS

FIGS. 1a–c are schematic representations of optical pulses incident on an optically thick spectral hole-burning material to form a temporal hologram under different conditions, where FIG. 1a illustrates writing the hologram with two light pulses separated in time, FIG. 1b illustrates how reading with the earlier pulse F recreates the later pulse G, and FIG. 1c illustrates how reading with the later pulse G does not produce any diffracted pulse;

FIG. 2a is a schematic diagram of an experimental arrangement used in demonstrating operation of the invention wherein light from two objects, a front object and a rear object, is separately recorded in a storage medium, with read out of "after" scattered light using a read out pulse coinciding with the direction of the original reference pulse;

FIG. 2b is similar to that of FIG. 2a, except with read out of the "before" scattered light using a read out pulse opposite in direction to the original reference pulse;

FIGS. 3a and 3b are photographs of the holographic reconstruction of the two objects employed in FIG. 2a.

BEST MODES FOR CARRYING OUT THE INVENTION

Figure 3B:
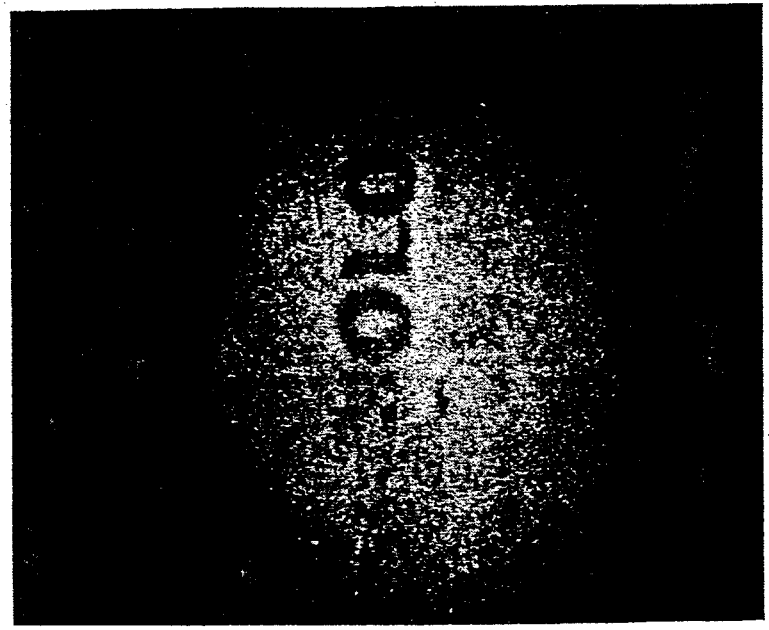

Consider two optical pulses incident on a holographic recording medium 10 as shown in FIG. 1. Let pulse F arrive $T_0$ seconds before pulse G (FIG. 1a). If photographic film is used as the recording medium, then an interference pattern will be recorded only if the pulses overlap with each other at least partially in time. However, let the photographic film be replaced by a bank of resonators such as atoms, with each atom tuned to a slightly different optical frequency $\omega_j$. In this case, the interference pattern of the two optical pulses F and G can be recorded even if the pulses are never present in the material at the same time.

If the optical pulse F is sufficiently brief, then its frequency spread will be wide enough to excite all of the atoms, much as a brief kick to a piano will excite all of the piano's strings. Each atom will continue to ring at its own natural frequency $\omega_j$. After a delay time $T_0$, the second light pulse G arrives, and it will transfer energy either into or out of the jth atom, depending on the relative phase between the optical electric field of G and the phase $\phi_j = \omega_j T_0$ of the still-ringing atom. Because each atom's phase depends on its particular resonant frequency $\omega j$, a given time delay $T_0$ between the two incident light pulses will produce a unique pattern of excited and unexcited atoms in frequency space.

After interacting with both of the light pulses F and G, let the absorption of the jth atom be semi-permanently altered by an amount proportional to the atom's final energy (by a mechanism described below). If the now-altered atoms are illuminated by a replica of pulse F (FIG. 1b), they will absorb and re-radiate light, again at the frequencies $\omega_j$ appropriate to each atom. At first, the phases of the re-radiated light will be incoherent, but after a time of exactly $T_0$, the phases of the different frequencies come together to reproduce coherently a duplicate of the pulse G. It can be shown, however, that application of a replica of pulse G to the altered atoms causes a re-radiation of light that loses rather than gains phase coherence with the passage of time in the direction of pulse F (FIG. 1c). Unlike conventional off-axis holography, where either light beam can be used to reconstruct the other, the bank of atoms here records the direction of time's arrow.

In fact, as described below, it is possible to reproduce an image of the scattered light that strikes the hologram 10 before the reference pulse arrives. To produce such an image, the hologram 10 is read out by a readout pulse applied in the opposite direction to the original reference pulse: reversing the direction of the readout pulse reverses the relative phase relation of the re-radiated light, and thereby leads to the recreation of the "before" rather than "after" scattered light.

Now consider illuminating an entire scene with a pulsed laser. Record the reflected light G using a bank of tuned resonators, and let a reference pulse F also illuminate the resonators, as described above. If the reference pulse arrives at the resonators before any of the reflected light, then the entire scene can be recalled by simply reading with another reference pulse. But if the initial reference pulse is delayed so that it arrives after some of the reflected light, then reading (with another reference pulse) will only recreate the parts of the image that arrived after that first reference pulse, which are the parts of the scene that were located farthest from the resonators. For example, if the scene consisted of the street view of a bookshop, then, with a suitably timed reference pulse, the reconstructed image would show the books on display deep inside the store, and would not show the reflections off the shop's front window.

A bank of narrow-band resonators 10' (FIGS. 2a and 2b) can be constructed, for example, by doping a solid block of polystyrene with the organic dye protoporphyrin. Each dye molecule acts as a lightly damped resonator, but because of inhomogeneities in the plastic matrix, each dye molecule has a slightly different resonant frequency. When illuminated by narrow-band light of frequency $\omega$, the molecules that happen to be in resonance with the light become excited. A fraction of these excited molecules subsequently relaxes into a metastable state (for example, a tautomerization of the original molecule). Once in this transformed state, the molecule's absorption is shifted to a completely different spectral region, so a narrow "hole" is burned into the sample's absorption spectrum at the frequency This spectral hole remains as long as the sample is kept cold. If cooled to a temperature of 2K, the phase-relaxation time, $T_2$, of the molecule's upper level becomes quite long ($T_2 \approx 1$ ns), so that the absorption hole has a narrow homogeneous spectral width of $\Delta \omega = 1/(\pi T_2) \approx 0.01$ cm$^{-1}$. A polystyrene matrix can cause the net absorption spectrum of all of the molecules to form an inhomogeneously broadened band extending over a range of $\approx 200$ cm$^{-1}$. Consequently, such a material resembles a bank of 200/0.01=20,000 narrow-band resonators, and this "spectral-hole-burning" material may be used to record and store the spectral (and, as will be shown below, spatial) contents of an incident light beam.

The spectral-hole-burning material requires use of a material the molecules of which continue vibrating between pulses from the laser. A long vibrating time means a narrow spectral line. While most molecules embedded in a plastic matrix damp out rather quickly, certain molecules unexpectedly continue to "ring" for as long as 1 ns when cooled to 2K.

In recording the hologram, the first pulse of light sets the dye molecules to vibrating. The second pulse of light transfers energy to a certain fraction of them, as described above.

The example given above is based on protoporphyrin embedded in a polystyrene matrix. Any matrix material that is amorphous (no long-range crystalline order) may be used in the practice of the invention; amorphous materials, due to their very nature, provide a non-uniform environment to the doped atoms or molecules, which causes a range of shifts in the optical frequency of the resonator. Further, crystals with impurities are also suitably employed in the practice of the invention, since impurities can occupy many different locations in the crystal. Each different location presents a different environment to the impurity, and so shifts the impurity's absorption by a different amount.

Examples of dyes and matrix materials include those listed in the Table below.

TABLE

| Typical Hole-Burning Materials. | |
|---|---|
| Dye | Matrix |
| Protoporphyrin | Polystyrene |
| Octaethylporphyrin | Polystyrene or polymethylmethacrylate |
| Chlorine | Polyvinylbutyral or polystyrene |
| Sm$^{2+}$ ions | SrFCl$_{0.5}$Br$_{0.5}$ single crystal |
| Color centers created by neutron irradiation (and annealing) | Sapphire crystals |
| absorbing molecules | spheres providing a resonant optical cavity* |

*As an example, the spheres (mean radius of about 1.44 μm) are filled with a dye, such as Nile Red.

The coherent light employed in storing the image may be pulsed or continuous. The time between the first and second pulses must be shorter than the phase relaxation time $T_2$. (In the present invention, $T_2 = 1$ nsec.) This can be accomplished by delaying one beam (object beam or reference beam) with respect to the other beam. If continuous coherent light of sufficiently short coherence length (e.g., coherent light from a broad band dye laser) is used, it may be delayed and, treated as if it were pulsed.

The speed of the "shutter" that has been formed by using spectral hole-burning materials is determined by the smaller of the following two spectral widths: the spectral width of the laser or the spectral width (the inhomogeneous linewidth) of the recording material. For example, if inhomogeneities in the recording material give it an effective absorption linewidth of 200 cm$^{-1}$, but the laser line-width is only 100 cm$^{-1}$ wide, then half of the material's linewidth will not be used and will be wasted, and in this example, the speed of the shutter is determined by the laser and not by the material. The wider the band, the faster the speed.

Stored information is read out by sending in one pulse; a second pulse will be emitted with the same time delay with which it was recorded.

It will be appreciated that the foregoing description is for one particular geometry. The Example below provides a more detailed description of this particular geometry. Other geometries may be constructed which accomplish the same result.

Finally, it is emphasized that the difference between the present invention, which employs spectral hole-burning materials, and previous holographic and non-holographic methods is that the reference beam and the image-bearing beam should not arrive at the same place at the same time in order to record the information.

EXAMPLE

A 3-mm-thick block of polystyrene was doped with protoporphyrin at a concentration of 10$^{-3}$ mol/l to form a stortoporphyrin medium 10'. The useful sample area was 4 cm$^2$. The sample 10' was immersed in liquid helium, and the helium vapors were pumped to reduce the temperature to 2K. The peak of the broad absorption feature was at $\lambda = 621$ nm, at which the optical density was 1.6.

The apparatus employed in this example is shown in FIG. 2a. The light source 12 was a continuous-wave mode-locked Nd:YAG laser 12a (Coherent Antares 76s) which synchronously pumped a tunable dye laser 12b (Coherent 701) to produce pulses having an intensity width of 8 ps full width at half maximum (FWHM). (These pulses are not transform-limited; they have a coherence width of only 0.5 ps.) The repetition rate of the laser pulses was 76 MHz. A quarterwave plate 13 converted the beam 12 from linear polarization to circular polarization. The advantage of using circularly polarized light is that it excites all of the dye molecules, irrespective of their alignment in the polymer, and so produces a larger signal. In contrast, linearly polarized light would excite only those dye molecules that were not aligned perpendicular to the axis of polarization. Those dye molecules aligned primarily perpendicular to the axis of polarization would be "wasted".

A beamsplitter 14 divided the beam from the picosecond dye laser 12a into a reference beam 16 and a separate (object) beam 18 to illuminate the various objects 20a, 20b in the scene. The reference beam 16 was expanded by a telescope (not shown) to illuminate the entire polystyrene block 10'. Scattered light from the illuminated objects 20a, 20b simply propagated to the polystyrene block 10' with no intervening lens. The angle between the reference beam 16 and the image-bearing beam 18 was $\approx 14°$. A delay line 22 was used to adjust the time for the reference beam 16 to reach the polystyrene block 10'.

The recorded scene consisted of two objects 20a, 20b. The nearby object 20a was a 1.0-mm-thick glass slide with the letters "HOLO" attached to its front surface.

The distant object 20b was a white paper screen carrying the letters "GRAM", which was pressed against the back of the transparent slide, so the separation between the two objects was ≈1 mm. To increase the amount of light scattered by the slide, its front surface was coated with a frosting aerosol spray (New York Bronze Powder Co.). The slide was illuminated from the front. Of the scattered light from the slide reaching the polystyrene block, ≈80% came from the front sprayed surface of the slide, and only ≈20% came from the rear surface. Viewing the laser-illuminated slide by eye 24 from the position of the polystyrene block 10', one could clearly read the letters HOLO, but the intense glare from the front surface almost completely obscured the letters GRAM located near the back of the slide.

Light from the laser reached the front of the slide 5 ps before it reached the back of the slide. Consequently, light from the front of the slide reached the storage medium 10 ps (twice the glass travel-through time) before light from the back of the slide. In the first experiment, a hologram was recorded with the reference beam 16 timed to arrive before both of these object waves. In the second experiment, a hologram was recorded with the reference beam 16 carefully timed to arrive within the 10-ps interval between the two object waves.

The reference beam and the object beam each had an average intensity of 0.2 mW/cm$^2$ at the location of the storage medium. An exposure time of 2 to 3 minutes was needed to record a hologram with a fluence of 70 to 100 mJ/cm$^2$, corresponding to $10^{10}$ identical pairs of laser pulses. To write the first hologram, the laser wavelength was tuned to the absorption maximum of the medium at 621 nm (19,950 cm$^{-1}$). Because the absorption spectrum is 200 cm$^{-1}$ wide and the dye-laser pulses have a spectral bandwidth of only ≈30 cm$^{-1}$, the wavelength of the dye laser could be changed by ≈30 cm$^{-1}$ and then a new hologram could be stored in a "fresh" spectral region of the storage medium without affecting any previously stored holograms. The different holograms written at different center wavelengths were later selectively read out by simply adjusting the center wavelength of the reading dye-laser pulse. In the absence of all illumination, these holograms lasted for as long as the sample was kept cold.

Figure 3A:
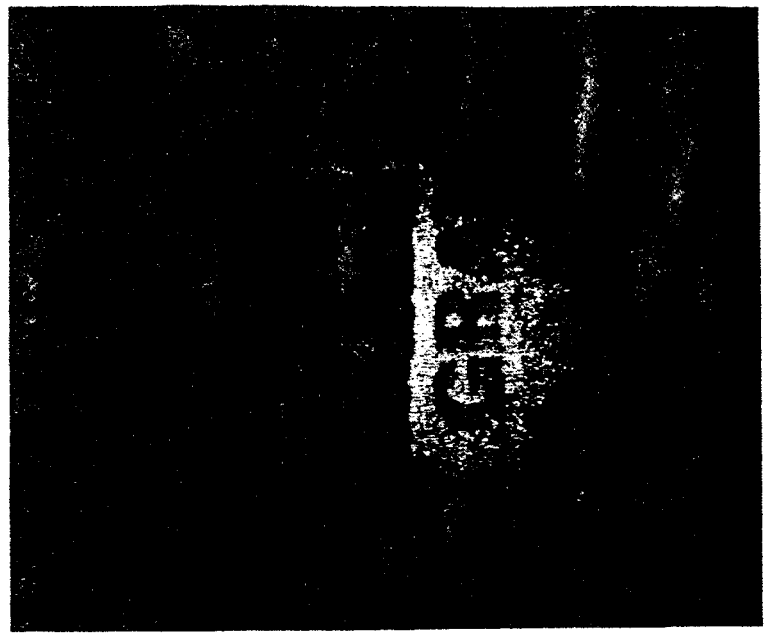

The holograms were read by blocking the light coming from the objects and illuminating the hologram with only the reference beam. FIG. 3a shows the reconstructed image when the hologram was recorded using a reference beam that arrived a few picoseconds before any of the light from the glass slide. The letters HOLO on the front of the slide are plainly visible, but the glare from the front of the slide almost obscures the letters GRAM near the back of the slide. FIG. 3b shows the reconstructed image when the reference beam pulse 16 was carefully set to arrive after light from the distant object 20b but before light from the nearby object 20a. Now, only the distant object 20b was reconstructed, and the nearby object 20a was eliminated.

It should be emphasized that the light from these objects 20a, 20b did not arrive at the polystyrene block 10' at the same time as light in the reference pulse 16 for the hologram to be recorded. In fact, because the coherence time of the light pulses was only 0.5 ps, and because the reference beam was set to arrive at the storage medium ≈5 ps before the light from the back of the slide, the reference and object beams could not have produced a conventional intensity interference pattern in the storage medium. It is noted that the maximum time delay permitted between the object and reference beams was $10^3$ ps and is set by the phase-decay time $T_2$ of the sample.

In the foregoing example, those objects that sent light to the hologram after the reference pulse had arrived could be selectively reconstructed. For some applications, however, it is desirable to do the opposite and recreate the light that arrived before the reference pulse. For example, consider the problem of imaging an object that is embedded in a scattering medium, such as a tumor embedded in breast tissue. Illuminate the tissue from behind with a short laser pulse. Light transmitted through the tissue without any scattering will emerge before light that has been multiply scattered by the tissue. Because the eye records all of this light, and because the scattered light overwhelms the unscattered light, the tumor remains unseen. But if light that arrived earlier at the eye could be selectively enhanced, then a shadow-gram of the tumor would become visible. Such an apparatus for accomplishing this is depicted in FIG. 2b.

This selection of early light over late light can be accomplished by simply altering the direction of the readout beam used in the example above. Instead of using a readout beam in the same direction as the reference beam, one should use a readout beam 26 that is directed exactly opposite to the direction of the original reference beam. A beamsplitter or mirror 28 directs the readout beam to the eye 24. This is the "four-wave mixing" geometry of traditional phase conjugation experiments, but with a spectral-hole-burning material, now only the light that arrived before the reference beam is holographically reconstructed in the final image. In this way, light scattered from backlighted tissue is eliminated, while light travelling directly through the tissue is preserved, forming the shadowgram of features embedded in the tissue.

INDUSTRIAL APPLICABILITY

The procedure of storing and recreating images of an object obscured by a light-scattering medium is expected to find a number of diverse uses, including medical diagnostics.

Thus, there has been disclosed a method of producing an image of an object obscured by a light-scattering medium. It will be readily apparent to those skilled in this art that various changes and modifications of an obvious nature may be made without departing from the spirit of the invention, and all such changes and modifications are considered to fall within the scope of the invention, as defined by the appended claims.

What is claimed is:

1. A method of recording an image of an object obscured by a light-scattering medium, comprising storing said image in a spectral hole-burning material by:
   (a) providing a spatially coherent source of light of sufficiently broad spectral content to illuminate said spectral hole-burning material, said source of light generating a source beam,
   (b) splitting said source beam into two portions, a reference beam and an object beam,
   (c) directing said reference beam onto said spectral hole-burning material,
   (d) directing said object beam onto said light-scattering medium to generate an image-bearing beam which is by predetermined choice either transmitted through said light-scattering medium or reflected thereby, said image-bearing beam comprising an image portion and an extraneous portion, (e) delaying one of said beams relative to the other of said beams for a period of time greater than the coherence time of said beams and less than the phase-decay time of said spectral hole burning material so that said reference beam arrives on said spectral hole-burning material at a time in between the arrival of said image portion and said extraneous portion of said image-bearing beam, and (f) directing said image-bearing beam onto said spectral hole-burning material in a manner so as to interact with said reference beam within a predetermined time related to $1/\Delta\omega$ for a time sufficient to alter said hole-burning material to cause the appearance of a plurality of narrow spectral holes, having a width $\Delta\omega$, in its absorption spectrum to thereby expose said hole-burning material and store said image therein.

2. The method of claim 1 wherein the relative path length of said reference beam and said image beam is adjustable.

3. The method of claim 1 wherein said object is embedded in said light-scattering medium.

4. The method of claim 1 wherein said object is in front of or behind said light-scattering medium.

5. The method of claim 1 wherein said image portion of said image-bearing beam arrives on said hole-burning material prior to said reference beam.

6. The method of claim 1 wherein said image portion of said image-bearing beam arrives on said hole-burning material subsequent to said reference beam.

7. The method of claim 1 wherein said hole burning material is selected from the group consisting of protoporphyrin/polystyrene, octaethylporphyrin/polystyrene, octaethylporphyrin/polymethylmethacrylate, chlorine/polyvinylbutyral, chlorine/polystyrene, $Sm^{2+}$ions/$SrFCl_{0.5}Br_{0.5}$ single crystal, color centers/sapphire crystals, and absorbing molecules dispersed in a matrix comprising spheres which provide a resonant optical cavity.

8. The method of claim 7 wherein said absorbing molecules comprise a dye, and wherein said spheres have a mean radius of about 1.44 $\mu$m and are filled with said dye.

9. The method of claim 8 wherein said dye is Nile Red.

10. The method of claim 7 wherein said molecules comprise a dye, and wherein said spheres have a mean radius of about 1.44 $\mu$m and are surrounded with said dye.

11. The method of claim 10 wherein said dye is Nile Red.

12. A method of producing an image of an object obscured by a light-scattering medium, comprising (a) storing said image in a spectral hole-burning material by:

(1) providing a spatially coherent source of light of sufficiently broad spectral content to illuminate said spectral hole-burning material, said source of light generating a source beam, (2) splitting said source beam into two portions, a reference beam and an object beam, (3) directing said reference beam onto said spectral hole-burning material.

(4) directing said object beam onto said light-scattering medium to generate an image-bearing beam which is by predetermined choice either transmitted through said light-scattering medium or reflected thereby, said image-bearing beam comprising an image portion and an extraneous portion, (5) delaying one of said beams relative to the other of said beams for a period of time greater than the coherence time of said beams and less than the phase-decay time of said spectral hole-burning material so that said reference beam arrives at said spectral hole-burning material at a time in between the arrival of said image portion and said extraneous portion of said image-bearing beam, and (6) directing said image-bearing beam onto said spectral hole-burning material in a manner so as to interact with said reference beam within a predetermined time related to $1/\Delta\omega$ for a time sufficient to alter said hole-burning material to cause the appearance of a plurality of narrow spectral holes, having a width $\Delta\omega$, in its absorption spectrum to thereby expose said hole-burning material and store said image therein; and (b) subsequently illuminating said exposed hole-burning material with a replica or counter-propagating conjugate replica of said reference beam and observing any diffracted light.

13. The method of claim 12 wherein the relative path length of said reference beam and said image beam is adjustable.

14. The method of claim 12 wherein said object is embedded in said light-scattering medium.

15. The method of claim 12 wherein said object is in front of or behind said light-scattering medium.

16. The method of claim 12 wherein said image portion of said image-bearing beam arrives on said hole-burning material prior to said reference beam.

17. The method of claim 12 wherein said image portion of said image-bearing beam arrives on said hole-burning material subsequent to said reference beam.

18. The method of claim 12 wherein said hole-burning material is selected from the group consisting of protoporphyrin/polystyrene, octaethylporphyrin/polystyrene, octaethylporphyrin/polymethylmethacrylate, chlorine/polyvinylbutyral, chlorine/polystyrene, $Sm^{2+}$ ions/$SrFCl_{0.5}Br_{0.5}$ single crystal, color centers/sapphire crystals, and absorbing molecules dispersed in a matrix comprising spheres which provide a resonant optical cavity.

19. The method of claim 18 wherein said absorbing molecules comprise a dye, and wherein said spheres have a mean radius of about 1.44 $\mu$m and are filled with said dye.

20. The method of claim 19 wherein said dye is Nile Red.

21. The method of claim 18 wherein said absorbing molecules comprise a dye, and wherein said spheres have a mean radius of about 1.44 $\mu$m and are surrounded with said dye.

22. The method of claim 21 wherein said dye is Nile Red.

* * * * *